US006558688B2

(12) United States Patent
Saishin et al.

(10) Patent No.: US 6,558,688 B2
(45) Date of Patent: May 6, 2003

(54) OCULAR TISSUE REGENERATION INDUCER

(75) Inventors: Mototsugu Saishin, 1-15-25 Hannan-cho, Abeno-ku, Osaka-City, Osaka 545-0021 (JP); Mitsuo Tsukamoto, 1-14-5, Ohiraki, Fukushima-ku, Osaka City, Osaka 553-0007 (JP); Takashi Makabe, Kurashiki (JP); Yoshimi Kakimaru, Kurashiki (JP); Takumi Fujitani, Osaka (JP); Tatsuhiko Higaki, Osaka (JP)

(73) Assignees: Kuraray Co., Ltd., Kurashiki (JP); Mototsugu Saishin, Osaka (JP); Mitsuo Tsukamoto, Osaka (JP)

( * ) Notice: Subject to any disclaimer, the term of this patent is extended or adjusted under 35 U.S.C. 154(b) by 0 days.

(21) Appl. No.: 09/768,625

(22) Filed: Jan. 25, 2001

(65) Prior Publication Data

US 2001/0038860 A1 Nov. 8, 2001

(30) Foreign Application Priority Data

Jan. 25, 2000 (JP) ........................................ 2000-015380

(51) Int. Cl.$^7$ .............................. A61K 9/06; A61K 9/08
(52) U.S. Cl. ..................... 424/427; 424/422; 424/78.04; 424/423; 424/426; 424/428; 424/400; 424/78.02
(58) Field of Search ............................... 424/78.04, 427, 424/422, 423, 426, 428, 400, 78.02

(56) References Cited

U.S. PATENT DOCUMENTS

| | | | | | |
|---|---|---|---|---|---|
| 3,947,573 | A | * | 3/1976 | Rankin ........................ | 424/78 |
| 4,407,792 | A | * | 10/1983 | Schoenwald et al. ......... | 424/81 |
| 4,409,205 | A | * | 10/1983 | Shively ....................... | 424/78 |
| 4,524,063 | A | * | 6/1985 | Wheeler ...................... | 424/78 |
| 5,104,787 | A | | 4/1992 | Lindstrom et al. | |
| 5,654,266 | A | | 8/1997 | Chen et al. | |
| 5,728,405 | A | | 3/1998 | McDonnell | |
| 5,767,105 | A | | 6/1998 | Peyman | |
| 5,770,607 | A | * | 6/1998 | Honbo et al. ................ | 514/302 |
| 5,876,709 | A | * | 3/1999 | Itoh et al. ................. | 424/78.04 |
| 5,942,487 | A | * | 8/1999 | Ogawa et al. ................. | 514/2 |

FOREIGN PATENT DOCUMENTS

| | | |
|---|---|---|
| EP | 0 641 563 A1 | 3/1995 |
| EP | 0641563 A1 * | 8/1995 |
| JP | 02255151 A | 10/1990 |
| JP | 403106814 A * | 5/1991 |
| JP | 05-117399 | 5/1992 |

* cited by examiner

Primary Examiner—Thurman K. Page
Assistant Examiner—Rachel M. Bennett
(74) Attorney, Agent, or Firm—Oblon, Spivak, McClelland, Maier & Neustadt, P.C.

(57) ABSTRACT

The invention relates to an ocular tissue regeneration inducer which comprises, as an active ingredient, a hydrophilic polymer mainly composed of alkylene glycol units or vinyl monomeric units having a nondissociating hydrophilic group. The composition can induce the regeneration of ocular tissues such as the cornea, the crystalline lens, and the vitreous body.

11 Claims, No Drawings

OCULAR TISSUE REGENERATION INDUCER

CROSS REFERENCES TO RELATED APPLICATIONS

This application claims priority to Japanese Patent Application No. 2000-15380, filed on Jan. 25, 2000, the entire content of which is incorporated herein by reference, the same as set forth at length.

BACKGROUND OF THE INVENTION

1. Field of the Invention

The present invention relates to ocular tissue regeneration inducers. The present invention also relates to methods for inducing the regeneration of ocular tissues.

2. Discussion of the Background

Among the ocular tissues, there are three highly transparent tissues, namely the cornea, crystalline lens and vitreous body. Conventionally, when the transparency of such tissues is found to be decreased, the part in question is surgically cut out, followed by grafting of the cornea from a donor in the case of the cornea, insertion of an intraocular lens made of a polymethyl methacrylate material in the case of the crystalline lens, or injection of air or a silicone oil in the case of the vitreous body. In particular, in the treatment of cataracts in which the crystalline lens becomes opaque, the method which comprises excising the crystalline lens and inserting an intraocular lens into the lens capsule has become widespread owing to the advancement in technique and the advent of improved intraocular lens, which is substitute for the crystalline lens (cf. JP Kokai H02-255151 and JP Kokai H05-117399, among others).

SUMMARY OF THE INVENTION

However, the above-mentioned method which inserting an intraocular lens cannot realize that accommodative function which is intrinsic in the crystalline lens to a satisfactory extent but, instead, has drawbacks, such as, for example, the range of accommodation is narrowed and the time required for focusing is prolonged.

Under these circumstances, there remains a need for a technique capable of recovering the functions intrinsic in the crystalline lens after excision of the opacified crystalline lens.

Accordingly, it is one object of the present invention to provide novel agents capable of inducing the regeneration of ocular tissues such as the cornea, the crystalline lens, and the vitreous body.

It is another object of the present invention to provide novel methods for inducing the regeneration of ocular tissues such as the cornea, the crystalline lens, and the vitreous body.

As a result of intensive investigations made by the present inventors in search of a physiologically active substance which, when administered into ocular tissues, can induce the regeneration of ocular tissues, it was unexpectedly found that when a hydrophilic polymer mainly composed of alkylene glycol units or vinyl monomeric units having a nondissociating hydrophilic group is administered into ocular tissues, the ocular tissues can be regenerated. Based on that finding, the present invention has now been completed.

Thus, in a first embodiment, the present invention provides an ocular tissue regeneration inducer which comprises, as an active ingredient, a hydrophilic polymer mainly composed of alkylene glycol units or vinyl monomeric units having a nondissociating hydrophilic group.

In a second embodiment, the present invention provides a method for inducing ocular tissue regeneration inducer, which comprises, administering to a subject in need thereof a composition, which comprise, as an active ingredient, a hydrophilic polymer mainly composed of alkylene glycol units or vinyl monomeric units having a nondissociating hydrophilic group.

The ocular tissue regeneration inducer and method of the invention are clinically useful for inducing the regeneration of ocular tissues such as the cornea, crystalline lens and vitreous body.

DETAILED DESCRIPTION OF THE PREFERRED EMBODIMENTS

Thus, in a first embodiment, the present invention provides an ocular tissue regeneration inducer which comprises, as an active ingredient, a hydrophilic polymer mainly composed of alkylene glycol units or vinyl monomeric units having a nondissociating hydrophilic group.

The ocular tissue regeneration inducer according to the invention comprises, as an active ingredient, a hydrophilic polymer mainly composed of alkylene glycol units or vinyl monomeric units having a nondissociating hydrophilic group (hereinafter, such polymer is sometimes referred to also as "hydrophilic polymer").

In describing the present invention, the term "vinyl monomeric units having a nondissociating hydrophilic group" (hereinafter sometimes referred to also as "hydrophilic vinyl monomeric units") means vinyl monomeric units free of dissociating groups capable of dissociating in the presence of water or moisture to generate an anion or cation (e.g. carboxyl group, sulfonic acid group, other acidic groups, salts thereof; alkaline groups such as amino group, or salts thereof) but having, within the molecule, a hydrophilic group or bond providing hydrophilic properties. As the nondissociating hydrophilic group, there may be mentioned a hydroxyl group, an amide bond, an acid anhydride group (group of the formula —CO—O—CO—) and the like. The hydrophilic vinyl monomeric units may have only one species selected from among a hydroxyl group, an amide group and an acid anhydride group or may have two or three of those species. Preferred as the hydrophilic group is a hydroxyl group and/or an amide bond.

The term "vinyl monomeric unit" as used herein means a monomeric unit derived from a monomer having a polymerizable double bond.

As the alkylene glycol units or hydrophilic vinyl monomeric units, which constitute the hydrophilic polymer mentioned above, there may be mentioned monomer units derived from alkylene glycols such as ethylene glycol and propylene glycol; vinyl alcohol; hydroxyl group-containing (meth)acrylic esters such as 2-hydroxyethyl (meth)acrylate, 2-hydroxypropyl (meth)acrylate, 3-hydroxypropyl (meth)acrylate, 2,3-dihydroxypropyl (meth)acrylate, polyethylene glycol mono(meth)acrylate, and polypropylene glycol mono (meth)acrylate; N-vinyllactams such as N-vinyl-2-piperidone, N-vinyl-2-pyrrolidone, N-vinyl-6-hexanelactam, N-vinyl-3-methyl-2-pyrrolidone, N-vinyl-3-methyl-2-piperidone, N-vinyl-3-methyl-6-hexanelactam, N-vinyl-4-methyl-2-pyrrolidone, N-vinyl-4-methyl-2-piperidone, N-vinyl-4-methyl-6-hexanelactam, N-vinyl-5-methyl-2-pyrrolidone, N-vinyl-5-methyl-2-piperidone, N-vinyl-5-methyl-6-hexanelactam, N-vinyl-6-methyl-6-hexanelactam, N-vinyl-3-ethyl-2-pyrrolidone, N-vinyl-4,5- dimethyl-2-pyrrolidone, and N-vinyl-5,5-dimethyl-2-pyrrolidone; (meth)acrylamides such as (meth)acrylamide, N,N-dimethyl(meth)acrylamide, N,N-diethyl(meth) acrylamide, N-hydroxymethyl(meth)acrylamide, N-(2-hydroxyethyl)(meth)acrylamide, and diacetone (meth) acrylamide; N-vinyl cyclic imides such as N-vinylsuccinimide and N-vinylmaleimide; N-vinylamides such as N-vinylformamide and N-vinylacetamide; 3-methylene-2-pyrrolidone; maleic anhydride; and so forth. These may be used singly or two or more of them may be used in combination. Preferred among these from the inducing ability of the ocular tissue regeneration are alkylene glycol units, vinyl alcohol units and N-vinyllactam units, more preferably vinyl alcohol units and N-vinyllactam units. Among the N-vinyllactam units, N-vinyl-2-pyrrolidone units are preferred.

The content of alkylene glycol units or hydrophilic vinyl monomeric units in the hydrophilic polymer is preferably within the range of 50 to 100 mole percent, more preferably within the range of 65 to 100 mole percent, still more preferably within the range of 75 to 100 mole percent. For adjusting the water solubility and/or viscosity, for instance, the hydrophilic polymer may contain hydrophobic monomeric units derived from alkyl (meth)acrylates such as methyl (meth)acrylate, butyl (meth)acrylate, and cyclohexyl (meth)acrylate; fluorine-containing (meth)acrylates such as trifluoroethyl (meth)acrylate; siloxane-containing (meth) acrylates such as tris(trimethylsiloxy)silylpropyl (meth) acrylate; vinyl esters such as vinyl acetate, vinyl butyrate, and vinyl hexanoate; and the like. The content of such hydrophobic monomeric units is preferably not more than 50 mole percent, more preferably not more than 35 mole percent, still more preferably not more than 25 mole percent.

From the viewpoint of the viscosity and ocular tissue regeneration inducing effect of the ocular tissue regeneration inducer, the weight average molecular weight of the hydrophilic polymer to be used in accordance with the invention is preferably within the range of 500 to 1,000,000, more preferably within the range of 700 to 1,000,000.

As the method of polymerization for obtaining the hydrophilic polymer to be used in the practice of the invention, there may be mentioned radical polymerization, ionic polymerization or polycondensation of such a monomer or monomers as mentioned above in the conventional manner by means of heat, light, radiation, or like energy. The mode of polymerization includes, but is not particularly limited to, bulk polymerization, solution polymerization, suspension polymerization, emulsion polymerization, and interfacial polymerization. The hydrophilic polymer obtained may further be modified by after-reaction or graft polymerization, for instance. For obtaining a hydrophilic polymer composed of vinyl alcohol units, it is preferably to subject a polymerizable composition comprising a vinyl ester such as vinyl acetate, vinyl butyrate, vinyl pivalate or vinyl versatate to polymerization and then saponify the polymerization product. The degree of saponification is preferably within the range of 50 to 100%, more preferably within the range of 65 to 100%, still more preferably within the range of 75 to 100%.

The ocular tissue regeneration inducer of the invention can be prepared by making up the above hydrophilic polymer into a pharmaceutical dosage form suited for local administration to the eye, for example an injection, aqueous ophthalmic solution, aqueous ophthalmic suspension, nonaqueous ophthalmic solution, nonaqueous ophthalmic suspension, or ophthalmic ointment, according to the conventional pharmaceutical practice. Aqueous preparations, such as an injection, aqueous ophthalmic solution and aqueous ophthalmic suspension, are preferred among them, however.

For facilitating the administration to ocular tissues and increasing the inducing effect of the ocular tissue regeneration, the above aqueous preparations preferably comprise 1 to 90 parts by weight of the hydrophilic polymer and 99 to 10 parts by weight of water, more preferably 3 to 85 parts by weight of the hydrophilic polymer and 97 to 15 parts by weight of water, still more preferably 5 to 80 parts by weight of the hydrophilic polymer and 95 to 20 parts by weight of water. When the content of the hydrophilic polymer is lower than 1 part by weight, the ocular tissue regeneration inducing effect will hardly be produced. When it is above 90 parts by weight, the ocular tissue regeneration inducer obtained will have an excessively high viscosity, and can hardly be injected into ocular tissues. For facilitating the administration using a thin needle, the aqueous preparations preferably have a viscosity of not higher than 50,000 cp, more preferably not higher than 30,000 cp, still more preferably not higher than 10,000 cp.

The method of preparing the above aqueous preparations is not particularly restricted but use may be made of the method comprising dissolving or suspending the aqueous polymer in an aqueous medium, together with an additive or additives, as desired, the method comprising adding a desired additive or additives to an aqueous solution or suspension containing the hydrophilic polymer as prepared in advance, or the method comprising dissolving or suspending the hydrophilic polymer in an aqueous medium prepared in advance and containing a desired additive or additives dissolved therein. In any case, it is preferable to produce the preparations under conditions such that the hydrophilic polymer and additive or additives will not be denatured.

Preferred as the aqueous medium to be used in producing the aqueous preparations is sterilized distilled water, which is generally used in producing ophthalmic preparations. The additive or additives mentioned above include isotonizing agents such as sodium chloride, potassium chloride, glycerol, and propylene glycol; buffers such as sodium phosphate, boric acid, $\epsilon$-aminocaproic acid, and monoethanolamine; stabilizers such as sodium edetate; preservatives such as benzalkonium chloride, methyl parahydroxybenzoate, ethyl parahydroxybenzoate, propyl palmitate, and chlorobutanol; surfactants such as polysorbate 80; and pH adjusting agents such as sodium hydroxide and hydrochloric acid; among others. These are added when necessary. It is also possible to add a nonaqueous solvent capable of dissolving the hydrophilic polymer to the above aqueous preparations according to the intended use and form thereof.

A hydrogel of the hydrophilic polymer in a cross linked form may also be used as the hydrophilic polymer in the aqueous preparations as long as a low viscosity can be retained. The cross linking agent for obtaining a cross linked hydrophilic polymer includes ethylene glycol di(meth) acrylate, diethylene glycol di(meth)acrylate, triethylene glycol di(meth)acrylate, propylene glycol di(meth)acrylate, trimethylolpropane tri(meth)acrylate, pentaerythritol tri(meth) acrylate, 1,4-butanediol di(meth)acrylate, 1,6-hexanediol di(meth)acrylate, glycerol di(meth)acrylate, divinylbenzene, diallyl phthalate, bisallyl carbonate and the like. These may be used singly or two or more of them may be used. The crosslinked hydrophilic polymer can be produced by polymerizing a polymerizable composition comprising such a crosslinking agent and the above-mentioned hydrophilic vinyl monomer or monomers. The crosslinking agent content on that occasion is preferably not more than 1% by weight relative to the total weight of the polymerizable composition. When that content is above 1% by weight, the viscosity of the aqueous preparation obtained will be so high that it becomes difficult to administer the preparation to ocular tissues.

When the ocular tissue regeneration inducer of the invention is to be administered into the lens capsule, the opacified lens substance is excised and then the composition is administered directly into the lens capsule using a syringe. More specifically, the administration into the lens capsule is carried out according to the following procedures (1) to (4). (1) After anesthetizing ocular tissues, an incision is made from the corneal margin and conjunctiva, and the transitional region from cornea to sclera is incised. (2) Through the incised wound, a small hole about 1 to 2 mm in size is made in the lens capsule, and the opaque lens substance is disrupted by sonication and removed by suction. (3) Through the incised wound and the hole in the lens capsule, the ocular tissue regeneration inducer is administered (filled) into the lens capsule. (4) The small hole made in the lens capsule is completely closed with a biocompatible patch, stopper, adhesive or the like so that the ocular tissue regeneration inducer may not leak out of the lens capsule. The dose of the ocular tissue regeneration inducer (hydrophilic polymer) to the lens capsule is preferably within the range of 0.05 to 2.5 g/administration, more preferably within the range of 0.1 to 2.0 g/administration. An injectable solution is preferred as the dosage form of the ocular tissue regeneration inducer, and the dose of the injectable solution may vary according to the structure of the lens capsule to be treated, but, generally, it is preferably within the range of 0.1 to 2.0 ml, more preferably within the range of 0.2 to 1.5 ml. When the dose is less than 0.1 ml, it is difficult to secure a space for crystalline lens regeneration within the lens capsule after removal of the lens substance, hence it is difficult to attain the effect of the crystalline lens regenerating. When it is higher than 2.0 ml, the dose may be excessive, possibly leading to fracture of the lens capsule. The frequency of administration may be appropriately selected taking into consideration the hydrophilic polymer species, which is the active ingredient in the ocular tissue regeneration inducer, the content thereof, the dosage form and other factors. Generally, however, one administration on the occasion of removal of the opaque lens substance will be sufficient.

In cases where the ocular tissue regeneration inducer of the invention is administered into the vitreous body cavity, the composition is administered directly into the vitreous body cavity after removal of the opacified vitreous body. Specifically, the composition is administered into the vitreous body cavity according to the following procedures (1) to (4). (1) After anesthetizing ocular tissues, the conjunctiva is incised at a site on one of the two sides of the superior straight muscle. (2) Through the incised wound, a small hole about 1 to 2 mm in size is made in the sclera, and the opaque vitreous body is removed. (3) Through the incised wound and the hole in the sclera, the ocular tissue regeneration inducer is administered (filled) into the vitreous body cavity. (4) The small hole is sutured. The dose of the ocular tissue regeneration inducer (hydrophilic polymer) to the vitreous body cavity is preferably within the range of 0.025 to 5.0 g/administration, more preferably within the range of 0.05 to 4.0 g/administration. An injectable solution is preferred as the dosage form of the ocular tissue regeneration inducer, and the dose of the injectable solution may vary according to the structure of the vitreous body cavity to be treated, but, generally, it is preferably within the range of 0.05 to 5.0 ml, more preferably within the range of 0.1 to 4.0 ml. When the dose is less than 0.05 ml, it is difficult to attain the vitreous body regenerating effect. When it is higher than 5.0 ml, the dose may be excessive, possibly leading to fracture of the crystalline lens and/or retina. The frequency of administration may be appropriately selected taking into consideration the hydrophilic polymer species, which is the active ingredient in the ocular tissue regeneration inducer, the content thereof, the dosage form and other factors. Generally, however, one administration on the occasion of removal of the opaque vitreous body will be sufficient.

In cases where the ocular tissue regeneration inducer of the invention is administered to the cornea, the dosage form and method of administration may appropriately be selected according to the symptom. For example, the ocular tissue regeneration inducer may be applied directly to the cornea and conjunctiva, or dropped into the eye in the form of an aqueous liquid, or applied directly into the anterior chamber with a syringe after anesthetizing ocular tissues. The dose of the ocular tissue regeneration inducer to the cornea may vary depending on the route of administration and the extent of damage of the cornea, but, generally, it is preferably within the range of 1 $\mu$g/administration to 0.1 g/administration. When the dose is less than 1 $\mu$g/administration, the regenerating effect can hardly be produced. When it is above 1 g/administration, the dose may be excessive, possibly leading to corneal tissue damage. The frequency of administration may be appropriately selected taking into consideration the hydrophilic polymer species, which is the active ingredient in the ocular tissue regeneration inducer, the content thereof, the dosage form and other factors. For example, the frequency may be once per several weeks, once a month or once per several months.

According to an alternative method of administration of the ocular tissue regeneration inducer, a sheet form of the ocular tissue regeneration inducer may be implanted after removal of the opaque cornea. The sheet form ocular tissue regeneration inducer can be produced, for example, by casting a polymerizable composition comprising a hydrophilic vinyl monomer(s) and a crosslinking agent into a sheet-shaped mold and polymerizing the same; by casting an aqueous solution containing the hydrophilic polymer into a sheet-shaped mold and irradiating the same with ultraviolet rays, radiation, or infrared rays; or by dissolving the hydrophilic polymer in a good solvent, casting the solution in a sheet-shaped mold and, after cooling, substituting an aqueous medium for the good solvent. The thickness and size of the sheet-form ocular tissue regeneration inducer and the method of implanting may appropriately selected depending on the symptom. In this case, the dose of the ocular tissue regeneration inducer may vary depending on the degree of corneal damage but, generally, it is preferably within the range of 0.05 to 5.0 g/administration. When the dose is less than 0.05 g/administration, the regenerating effect can hardly be produced and, when it is above 5.0 g/administration, the dose may be excessive, possibly leading to damage of normal corneal and conjunctival tissues. The frequency of administration may be appropriately selected taking into consideration the hydrophilic polymer species, which is the active ingredient in the ocular tissue regeneration inducer, the content thereof, the thickness and size and other factors. Generally, one administration on the occasion of removal of the opaque cornea will be sufficient.

Since the ocular tissue regeneration inducer of the present invention is directly administered or applied to or implanted into ocular tissues, as mentioned above, it is desirable that the composition be prepared under sterile conditions or sterilized prior to use by a predetermined method. From the operability viewpoint, it is preferable to prepare the composition under sterile conditions. Considering the operability on the occasion of administration to ocular tissues by means of a syringe, it is desirable that the composition be supplied in the form of a sealed vial, more preferably in the form of a sealed cartridges for injection.

As the diameter of the syringe needle to be used for the administration into the lens capsule, vitreous body cavity or anterior chamber decreases, the small hole required for the administration of the ocular tissue regeneration inducer becomes smaller, hence the influences on the visual function after administration becomes less. Accordingly, the use of a needle with a smaller diameter is preferred. The needle is preferably finer than 16G (gauge), more preferably finer than 18G, still more preferably finer than 20G.

For retaining the visual function even after direct administration of the ocular tissue regeneration inducer of the invention into ocular tissues following removal of infected (opaque) ocular tissues, it is desirable that the composition have a visible light transmittance of not less than 50%.

The hydrophilic polymer, which is the active ingredient according to the present invention, has so far been used as a material for medical use in the field of ophthalmology, for example as a contact lens material and it has thus been confirmed that it has no toxicity or irritancy to living organisms.

According to the present invention, an agent capable of inducing the regeneration of ocular tissues, such as the cornea, crystalline lens and vitreous body, is provided. Upon administration of the ocular tissue regeneration inducer of the present invention into ocular tissues, the ocular tissue at the site of administration is regenerated. In particular, when the ocular tissue regeneration inducer of the present invention is administered into the crystalline lens capsule, the protein (crystallin) constituting the crystalline lens is markedly regenerated. Therefore, the composition is clinically useful as a crystalline lens regeneration inducing agent.

Other features of the invention will become apparent in the course of the following descriptions of exemplary embodiments which are given for illustration of the invention and are not intended to be limiting thereof.

EXAMPLES

The following examples specifically illustrate the invention. They are, however, by no means limitative of the scope of the invention.

The product "OPEGUARD®-MA" used in the examples is an intraocular perfusate (aqueous solution) having the following composition: glucose, 1.5 mg/ml; sodium chloride, 6.6 mg/ml; potassium chloride, 0.36 mg/ml; calcium chloride, 0.18 mg/ml; magnesium sulfate, 0.3 mg/ml; and sodium hydrogen carbonate, 2.1 mg/ml. OPEGUARD® is a registered tradename.

Example 1

An ocular tissue regeneration inducer was prepared by dissolving 30 parts by weight of polyvinyl alcohol ("PVA 203," product of Kuraray Co., Ltd.; average molecular weight 15,000, saponification degree 88 mole percent), as the hydrophilic polymer, in 70 parts by weight of OPEGUARD®-MA (product of Senju Pharmaceutical Ltd.). This composition had a viscosity of 770 cp and a visible light transmittance of 99.1%.

Example 2

An ocular tissue regeneration inducer was prepared by dissolving 40 parts by weight of poly(N-vinyl-2-pyrrolidone) ("K-15," product of Gokyo Sangyo; average molecular weight 10,000), as the hydrophilic polymer, in 60 parts by weight of OPEGUARD®-MA (product of Senju Pharmaceutical Ltd.). This composition had a viscosity of 370 cp and a visible light transmittance of 87%.

Example 3

An ocular tissue regeneration inducer was prepared by dissolving 60 parts by weight of polyethylene glycol ("PEG #1000," product of Wako Pure Chemicals Industries, Ltd.; average molecular weight 1,000), as the hydrophilic polymer, in 40 parts by weight of OPEGUARD®-MA (product of Senju Pharmaceutical Ltd.). This composition had a viscosity of 440 cp and a visible light transmittance of 97%.

Test Example 1

The ocular tissue regeneration inducers prepared in Examples 1 to 3 were each sealed in cartridges for injection and then sterilized by autoclaving. The lens substance of each normal rabbit (male Japanese albino rabbit, weighing 2.5 to 3.0 kg) was excised by ultrasonic emulsification and suction, 0.3 ml of each ocular tissue regeneration inducer was injected into the lens capsule using a 24G needle, and the small hole formed was sealed with a silicone plug. The small hole in the lens capsule was not greater than 1 mm and no leakage of the ocular tissue regeneration inducer administered into the lens capsule was observed.

After the lapse of 6 months following administration of the ocular tissue regeneration inducer, the lens capsule and the contents thereof of each rabbit were surgically extracted and the extracted matter was homogenized in 6 ml of tris(hydroxymethyl)aminomethane-tris(hydroxymethyl) aminomethane hydrochloride buffer, and the homogenate was centrifuged. The supernatant obtained was assayed for protein concentration using a protein assay kit, product of Bio-Rad Laboratories Inc. As a result, the concentration was found to be 19.3 mg/ml in the case of administration of the ocular tissue regeneration inducer of Example 1, 22.4 mg/ml for the ocular tissue regeneration inducer of Example 2, and 13.7 mg/ml for the ocular tissue regeneration inducer of Example 3. For the normal rabbit lens, it was 25.1 mg/ml.

The regenerated protein was immunologically identified by ELISA by coating 96-well plates with 10 µg/well of each of the above supernatants and using mouse anti-bovine α-B-crystallin monoclonal antibody as a primary antibody, alkaline phosphatase-conjugated goat anti-mouse immunoglobulin G antibody as a secondary antibody and p-nitrophenyl phosphate (1 mg/ml) as a color forming reagent. Bovine serum albumin was used as a negative control. For the cases of administration of the ocular tissue regeneration inducers of Examples 1 to 3, color development was confirmed while, for the negative control bovine serum albumin, no color development was observed.

In the above Test Example 1, in all the cases where the ocular tissue regeneration inducers of Examples 1 to 3 of the invention were administered, protein regeneration was confirmed and the protein was immunologically proved to be the lens-constituting protein crystallin, indicating that the ocular tissue regeneration inducers of the present invention can induce the regeneration of the crystalline lens.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A method for inducing ocular tissue regeneration, comprising administering to a subject in need thereof and effective amount of an ocular tissue regeneration inducer, which comprises, as an active ingredient, a hydrophilic polymer mainly composed of monomeric units selected from the group consisting of alkylene glycol units, vinyl monomeric units having a nondissociating hydrophilic group, and mixtures thereof.

2. The method of claim 1, wherein said nondissociating hydrophilic group is selected from the group consisting of a hydroxyl group, an amide bond, and an acid anhydride group.

3. The method of claim 1, wherein said hydrophilic polymer is a polymer mainly composed of monomeric units selected from the group consisting of alkylene glycol units, vinyl alcohol units, N-vinyllactam units, and mixtures thereof.

4. The method of claim 1, wherein said hydrophilic polymer is a polymer mainly composed of monomeric units derived from monomers selected from the group consisting of ethylene glycol, propylene glycol, vinyl alcohol, 2-hydroxyethyl (meth)acrylate, 2-hydroxypropyl (meth)acrylate, 3-hydroxypropyl (meth)acrylate, 2,3-dihydroxypropyl (meth)acrylate, polyethylene glycol mono(meth)acrylate, polypropylene glycol mono(meth)acrylate, N-vinyl-2-piperidone, N-vinyl-2-pyrrolidone, N-vinyl-6-hexanelactam, N-vinyl-3-methyl-2-pyrrolidone, N-vinyl-3-methyl-2-piperidone, N-vinyl-3-methyl-6-hexanelactam, N-vinyl-4-methyl-2-pyrrolidone, N-vinyl-4-methyl-2-piperidone, N-vinyl-4-methyl-6-hexanelactam, N-vinyl-5-methyl-2-pyrrolidone, N-vinyl-5-methyl-2-piperidone, N-vinyl-5-methyl-6-hexanelactam, N-vinyl-6-methyl-6-hexanelactam, N-vinyl-3-ethyl-2-pyrrolidone, N-vinyl-4,5-dimethyl-2-pyrrolidone, N-vinyl-5,5-dimethyl-2-pyrrolidone, (meth)acrylamide, N,N-dimethyl(meth)acrylamide, N,N-diethyl(meth)acrylamide, N-hydroxymethyl(meth)acrylamide, N-(2-hydroxyethyl)(meth)acrylamide, diacetone (meth)acrylamide, N-vinylsuccinimide, N-vinylmaleimide, N-vinylformamide, N-vinylacetamide; 3-methylene-2-pyrrolidone, maleic anhydride, and mixtures thereof.

5. The method of claim 1, wherein said hydrophilic polymer has a weight average molecular weight of 500 to 1,000,000.

6. The method of claim 1, which comprises: (a) 1 to 90 parts by weight of said hydrophilic polymer mainly composed of monomeric units selected from the group consisting of alkylene glycol units, vinyl monomeric units having a nondissociating hydrophilic group, and mixtures thereof, and (b) 99 to 10 parts by weight of water.

7. The method of claim 1, wherein said monomeric units selected from the group consisting of alkylene glycol units, vinyl monomeric units having a nondissociating hydrophilic group, and mixtures thereof comprise 50 to 100 mole percent of said hydrophilic polymer.

8. The method of claim 1, which has viscosity of less than or equal to 50,000 cp.

9. The method of claim 1, wherein said ocular tissue regeneration inducer is administered to the lens capsule, the vitreous body, or the cornea, of said subject in need thereof.

10. The method of claim 1, wherein said ocular tissue regeneration inducer is administered to the lens capsule, of said subject in need thereof.

11. The method of claim 1, wherein said ocular tissue regeneration inducer induces regeneration of a crystalline lens of said subject in need thereof.

* * * * *